(12) United States Patent
Lachmann et al.

(10) Patent No.: US 10,584,163 B2
(45) Date of Patent: Mar. 10, 2020

(54) MONOCLONAL ANTIBODY AGAINST HUMAN TAU PROTEIN

(71) Applicant: AJ ROBOSCREEN GMBH, Leipzig (DE)

(72) Inventors: Ingolf Lachmann, Leipzig (DE); Max Holzer, Leipzig (DE); Piotr Lewczuk, Hemhofen (DE); Johannes Kornhuber, Nuremberg (DE); Armand Perret-Liaudet, Lyons (FR); Katharina Waniek, Leipzig (DE)

(73) Assignee: AJ ROBOSCREEN GMBH, Leipzig (DE)

(*) Notice: Subject to any disclaimer, the term of this patent is extended or adjusted under 35 U.S.C. 154(b) by 0 days.

(21) Appl. No.: 15/511,250

(22) PCT Filed: Sep. 17, 2015

(86) PCT No.: PCT/DE2015/100394
§ 371 (c)(1),
(2) Date: Mar. 15, 2017

(87) PCT Pub. No.: WO2016/041553
PCT Pub. Date: Mar. 24, 2016

(65) Prior Publication Data
US 2017/0260262 A1 Sep. 14, 2017

(30) Foreign Application Priority Data
Sep. 18, 2014 (DE) .......... 10 2014 013 571

(51) Int. Cl.
*C07K 16/18* (2006.01)
*G01N 33/68* (2006.01)

(52) U.S. Cl.
CPC .......... *C07K 16/18* (2013.01); *G01N 33/6896* (2013.01); *C07K 2317/34* (2013.01); *G01N 2333/4709* (2013.01); *G01N 2800/2821* (2013.01)

(58) Field of Classification Search
CPC .............. C07K 16/18; C07K 2317/34; G01N 33/6896; G01N 2333/4709; G01N 2800/2821
See application file for complete search history.

(56) References Cited

U.S. PATENT DOCUMENTS

| 5,994,084 A | 11/1999 | Anderton et al. |
| 6,232,437 B1 | 5/2001 | Vandermeeren et al. |
| 6,238,892 B1 | 5/2001 | Mercken et al. |
| 2012/0295852 A1 | 11/2012 | Moskal |
| 2014/0294731 A1 | 10/2014 | Pfeifer et al. |
| 2015/0344553 A1 | 12/2015 | Weinreb et al. |

FOREIGN PATENT DOCUMENTS

| WO | 95/05466 A1 | 2/1995 | |
| WO | WO-9517429 A1 * | 6/1995 | ......... C07K 14/4711 |
| WO | WO-0155725 A2 * | 8/2001 | ......... C07K 14/4711 |
| WO | 2014/100600 A2 | 6/2014 | |

OTHER PUBLICATIONS

Köhler G and Milstein C. Continuous cultures of fused cells secreting antibody of predefined specificity. 256, 495-497. (Year: 1975).*
Cell Fusion/Hybridoma Production Protocol. Wagner Lab, Cornell University and Baldwin Lab, U Mass, Jul. 2008, www.umass.edu/vetimm/docs/Wagner_Hybridoma.pdf, 4 pages. (Year: 2008).*
International Search Report for PCT/DE2015/100394, dated Oct. 10, 2016, 2 pages.
Binder et al.; "The Distribution of Tau in the Mammalian Central Nervous System;" The Journal of Cell Biology; vol. 101; Oct. 1985; pp. 1371-1378.
Ghoshal; "Tau Conformational Changes Correapond to Impairments of Episodic Memory in Mild Cognitive Impairment and Alzheimer's Disease;" Experimental Neurology; vol. 177; No. 2; Oct. 1, 2002; pp. 475-493.
Köhler et al.; "Continuous cultures of fused cells secreting antibody of predefined specificity;" Nature; vol. 256; Aug. 7, 1975; pp. 495-497.
Lewczuk et al.; Neurochemical dementia diagnostics in Alzheimer's disease: where are we now and where are we going?; Expert Rev. Proteomics 8(4); 2011, pp. 447-458.
Kosik et al.; "Tau In Situ Hybridization in Normal and Alzheimer Brain: Localization in the Somatodendritic Compartment;" Annals of Neurology; vol. 26; No. 3; Sep. 1989; pp. 352-361.
Goedert et al.; "Multiple Isoforms of Human Microtubule-Associated Protein Tau: Sequences and Localization in Neurofibrillary Tangles of Alzheimer's Disease;" Neuron; vol. 3; Oct. 1989; pp. 519-526.
Neve et al.; "Identification of cDNA clones for the human microtubule-associated protein tau and chromosomal localization of the genes for tau and microtubule-associated protein 2;" Molecular Brain Research; 1; Elsevier; Sep. 1986; pp. 271-280.
Goedert et al.; "Molecular characterization of microtubule-associated proteins tau and MAP2;" TINS; vol. 14; No. 5; 1991; pp. 193-199.
Goedert; "Tau protein and the neurofibrillary pathology of Alzheimer's disease;" TINS; vol. 16; No. 11; 1993; pp. 460-465.
Hutton et al.; "Association of missense and 5'-splice-site mutations in tau with the inherited dementia FTDP-17;" Nature; vol. 393; Jun. 18, 1998; pp. 702-705.
Bugiani et al.; "Frontotemporal Dementia and Corticobasal Degeneration in a Family with a P301S Mutation in Tau;" Journal of Neuropathology and Experimental Neurology; vol. 58; No. 6; Jun. 1999; pp. 667-677.

(Continued)

Primary Examiner — Kimberly Ballard
(74) Attorney, Agent, or Firm — Abel Schillinger, LLP

(57) ABSTRACT

The invention relates to the monoclonal antibody 1G2, the hybridoma cell line H-1 G2 characterized by DSM ACC3248, and the epitope TPP comprising the amino acids threonine, proline, proline. The invention further relates to a method for producing a monoclonal antibody against a TAU protein fraction that is non-phosphorylated in positions T175 and/or T181 and/or T231. The invention also describes uses of the monoclonal antibody 1 G2 as well as an immunochemical detection system and the uses thereof. The invention finally describes the use of the immunochemical detection system for diagnosing Alzheimer's disease in humans.

20 Claims, 4 Drawing Sheets

Specification includes a Sequence Listing.

(56) References Cited

OTHER PUBLICATIONS

Eidenmüller et al.; "Structural and Functional Implications of Tau Hyper;hosphorylation: Information from Phosphorylation-Mimicking Mutated Tau Proteins;" Biochemistry; vol. 39; No. 43; 2000; pp. 13166-13175.

Bancher et al.; "Accumulation of abnormally phosphorylated tau precedes the formation of neurofibrillary tangles in Alzheimer's disease;" Brain Research; Elsevier; 477; 1989; pp. 90-99.

Friedhoff et al.; "A nucleated assembly mechanism of Alzheimer paired helical filaments;" Proc. Natl. Acad. Sci. USA; Neurobiology; vol. 95;1998; pp. 15712-15717.

Chirita et al.; "Evidence for an Intermediate in Tau filament Formation;" Biochemistry; vol. 43; No. 6; 2004; pp. 1704-1714.

Berriman et al.; "Tau filaments from human brain and from in vitro assembly of recombinant protein show cross-β structure;" PNAS; vol. 100; No. 15; 2003; pp. 9034-9038.

Lashuel; "Membrane Permeabilization: A Commmon Mechanism in Protein-Misfolding Diseases;" Sci. Aging Knowl. Environ.; vol. 2005; Issue 38; 2005; p. pe28; 13 pages.

Maeda et al.; "Granular Tau Oligomers as Intermediates of Tau Filaments;" American Chemical Society; Biochemistry; vol. 46; No. 12; 2007; pp. 3856-3861.

Caughey et al.; "Protofibrils, Pores, Fibrils, and Neurodegeneration: Separating the Responsible Protein Aggregates from the Innocent Bystanders;" Annu. Rev. Neurosci.; vol. 26; 2003; pp. 267-298.

Blennow et al.; "Clinical utility of cerebrospinal fluid biomarkers in the diagnosis of early Alzheimer's disease;" Alzheimers Dement. ;11(1); Jan. 2015; pp. 58-69; Author manuscript: 23 pages.

Braithwaite et al.; "Protein Phosphatases and Alzheimer's Disease;" Progress in Molecular Biology and Translational Science; vol. 106; 2012, Elsevier Inc.; pp. 343-379.

Albert et al.; "The diagnosis of mild cognitive impairment due to Alzheimer's disease: Recommendations from the gational Institute on Aging-Alzheimer's Association workgroups on diagnostic guidelines for Alzheimer's disease;" Elsevier; Alzheimer's & Dementia; vol. 7; 2011; pp. 270-279.

Mc Khann et al.; "The diagnosis of dementia due to Alzheimer's disease: Recommendations from the National Institute on Aging-Alzheimer's Association workgroups on diagnostic guidelines for Alzheimer's disease;" Elsevier; Alzheimer's & Dementia; vol. 7; 2011; pp. 263-269.

Littlefield; "Selection of Hybride from Matings of Fibroblasts in vitro and Their Presumed Recombinants;" Science; vol. 145; Aug. 14, 1964; pp. 709-710; downloaded from science.sciencemag.org on May 5, 2017; 3 pages.

Osman et al.; "A monoclonal antibody that recognizes a potential coeliac-toxic repetitive pentapeptide epitope in gliadins;" European Journal of Gastroenterology & Hepatology; vol. 13; 2001; pp. 1-5; Article No. 5879; 5 pages.

Folstein et al.; "'Mini-Mental State' A Practical Method for Grading the Cognitive State of Patients for the Clinician;" J. Psychiat. Res.; vol. 12; 1975; pp. 189-198.

Chemicon International a Serologicals Company; "Mouse Anti-Tau-1 Monoclonal Antibody", 3 pgs, Dec. 2, 2005.

Lewczuk et al.: "Non-Phosphorylated Tau as a Potential Biomarker of Alzheimer's Disease: Analytical and Diagnostic Characterization", Journal of Alzheimer's Disease 55 (2017) 159-170.

Doyle et al.; "Autoantigenesis: the evolution of protein modifications in autoimmune disease", SciVerse ScienceDirect, Current Opinion in Immunology 2012, 24:112-118.

Pushko P et al.: "Identification of Hepatitis B Virus Core Protein Regions Exposed or Internalized at the Surface of HBCAG Par Ticles by Scanning With Monoclonal Antibodies", Virology, Elsevier, Amsterdam, NL, Bd. 202, Nr. 2, Aug. 1, 1994 (Aug. 1, 1994), pp. 912-920.

Anonymous: "Anti-Tau (T175) Antibody", Apr. 29, 2014 (Apr. 29, 2014).

Joery Goossens et al.: "No added diagnostic value of non-phosphorylated tau fraction (p-taurel) in CSF as a biomarker for diff erential dementia diagnosis", Alzheimer's Research & Therapy, Bd. 9, Nr. 1, Jul. 14, 2017 (Jul. 14, 2017), pp. 1-7.

Rosenberg Amy S: "Effects of protein aggregates: An immunologic perspective", The AAPS Journal, Springer New York, New York, Bd. 8, Nr. 3, Sep. 1, 2006 (Sep. 1, 2006), pp. E501-E507.

Ebru Ercan et al.: "A validated antibody panel for the characterization of tau post-translational modifications", Molecular Neurodegeneration, Bd. 12, Nr. 1, Nov. 21, 2017 (Nov. 21, 2017).

Ermann Natalia et al.: "CSF nonphosphorylated Tau as a Biomarker for the discrimination of AD from CJD.", Annals of Clinical and Tr Anslational Neurology Jul. 2018, Bd. 5, Nr. 7, Jul. 2018 (Jul. 2018), pp. 883-887.

Molinuevo Jose Luis et al.: "Current state of Alzheimer's fluid biomarkers", Acta Neuropathologica, Springer Verlag, Berlin, DE, Bd. 136, Nr. 6, Nov. 28, 2018 (Nov. 28, 2018), pp. 821-853.

Calderon-Garciduenas Lilian et al.: "Non-Phosphorylated Tau in Cerebrospinal Fluid is a Marker of Alzheimer's Disease Continuum in Young Urbanites Exposed to Air Pollution.", Journal of Alzheimer's Disease : JAD 2018, Ed. 66, Nr. 4, 2018, pp. 1437-1451.

Illenberger S. et al.: "The endogenous and cell cycle-dependent phosphorylation of tau protein in living cells: Implications for Alzheimer's disease", Molecular Biology of the Cell, Americn Society for Cell Biology, US, Bd. 9, Jun. 1, 1998 (Jun. 1, 1998), pp. 1495-1512.

Cambridge University Press; "Recombinant Antibodies for Immunotherapy;" ed. Melvine Little, Chapter 1, pp. 3-19, 2009.

\* cited by examiner

MONOCLONAL ANTIBODY AGAINST HUMAN TAU PROTEIN

BACKGROUND OF THE INVENTION

1. Field of the Invention

The present invention relates to a monoclonal antibody against human TAU protein, a method for the preparation thereof and also uses of the monoclonal antibody.

2. Discussion of Background Information

Monoclonal antibodies are immunologically active proteins, which are produced from a cell line, which arise from a single B-lymphocyte. Monoclonal antibodies are directed against an individual epitope. In diagnostics and research, monoclonal antibodies consequently play a major role, since they can bind with high specificity to a number of molecules, wherein the binding can be demonstrated by different techniques.

Methods for preparing monoclonal antibodies go back to studies by Köhler & Milstein [1] and have been widely researched and enhanced in recent years and decades. Monoclonal antibodies are indispensable as detectors for epitopes on cell surfaces.

They are also used in a variety of ways in diagnostics of animal and human diseases as constituents of therapeutic agents.

Alzheimer's disease (morbus Alzheimer) is characterized by the occurrence of two forms of protein aggregates in the brain of affected patients. Extracellular amyloid plaques and intraneuronal clumping of the TAU protein in the isocortex are pathological markers for the post mortem diagnosis of Alzheimer's disease. Both protein constituents of these deposits, the beta-amyloid peptide and the TAU protein, may serve as potential biomarkers for diagnosis of the disease. A decrease in the beta-amyloid peptide content and an increase in TAU protein and their phosphorylated form at amino acid Ti 81 in cerebrospinal fluid are characteristics of progressive Alzheimer's disease (Lewczuk & Kornhuber [2]) and can support a clinical diagnosis.

The TAU protein exists in the human brain in six isoforms, which are expressed in a development-dependent manner (Kosik et al. [3]; Goedert et al. [4]). The so-called splicing isoforms originate from a single TAU gene comprising in total 14 exons. The gene locus is found on the long arm of chromosome 17 (Neve et al. [5]). The molecular heterogeneity of TAU expression in the central nervous system is caused by alternative splicing of exons 2, 3 and 10 (Goedert et al. [6]). In this case, two sequences of 29 amino acids each are inserted in the N-terminal half or an additional microtubule binding in the C-terminal region.

FIG. 1 shows for this purpose a schematic representation of the TAU isoforms. The individual isoforms are designated by Goedert [7]. The alternatively used exons 2, 3 and 10 are highlighted. The localization of the microtubule binding repeats is represented in black.

Due to its amino acid composition, the TAU protein is hydrophilic, highly soluble and is present in a native unfolded state (without secondary structure). The triggers which cause the aggregation of the TAU protein in vivo under pathological conditions are unknown. It is assumed that the conformational modifications or posttranslational modifications may be caused by interactions with other proteins and/or the aggregation of the TAU protein can arise by mutations (in the case of FTDP-17) in the TAU gene. It could be shown in vitro that most of the exonic mutations in the TAU gene impair the ability of the TAU protein to bind to microtubules, to increase its tendency to aggregate or to lead to an altered ratio of the TAU isoforms (Hutton et al. [8]; Bugiani et al. [9]). With increasing degree of phosphorylation and in hyperphosphorylation of the TAU protein, there is a decrease in affinity to bind to microtubules and to mediate microtubule polymerization (Eidenmüller et al. [10]). Mutations and post-translational hyperphosphorylation can therefore lead to the accumulation of hyperphosphorylated TAU protein in the cytoplasm of neurons. This accumulation of hyperphosphorylated TAU protein in soma is accepted as the first detectable step of TAU aggregation (Bancher et al. [11]). It is assumed that the accumulated, hyperphosphorylated TAU monomers in an entropy-driven nucleation-forming condensation mechanism aggregate via intermediates to TAU filaments (Friedhoff et al. [12]; Chirita & Kuret [13]). This leads to a conformational change from the so-called "random coil" to the beta-sheet secondary structure in the region of the microtubule binding region (Berriman et al. [14]). After the conformational change, the time-determining step of TAU aggregation leads to the formation of a dimer, presumably due to the hydrophobic interaction of the beta-sheet structures of both molecules. In this case, the two TAU molecules are superimposed, i.e. transposed by 90° via their beta-sheet structures (cross-β state). Via the formation of intermolecular disulfide and hydrogen bonds, the dimers can be stabilized. The so-called nucleus or condensation nucleus is formed by the assembly of 4 to 7 dimers, to which further dimers accumulate.

FIG. 2 shows for this purpose the aggregation of amyloidogenic proteins and formation of pores in the cell membrane. The aggregation of amyloidogenic proteins is presumably initiated by conformational changes in the protein monomer to form beta-sheet structures. During the time-determining step of protein aggregation, hydrophobic interactions occur between the formed beta-sheet structures of two monomers to form dimers. It is presumed that oligomeric amyloidogenic proteins can form in the cell membrane pores, which lead to a disruption of the membrane integrity (modified according to Lashuel [15]).

In this case, initially small granular TAU oligomers are formed, which consist of approx. 40 monomers (Maeda et al. [16]). By further deposition of dimers, larger protofibrillary oligomers then form from the granular TAU oligomers. TAU filaments then form from the protofibrillary oligomers by continued deposition of dimers. Several TAU filaments finally form the neurofibrillary bundles typical of tauopathies (Caughey & Lansbury [17]).

The relevance of TAU proteins is known in principle in the prior art. For instance, U.S. Pat. No. 6,232,437 B1 describes various TAU peptide epitopes in connection with the monoclonal antibody AT120, which reacts with both normal and abnormal phosphorylated TAU and recognizes a binding site of the amino acid sequence P218 to L224 of the TAU protein. U.S. Pat. No. 6,238,892 B1 further describes a monoclonal antibody AT8, which forms an immunological complex with a phosphorylated epitope of an antigen, which includes human abnormal phosphorylated TAU proteins.

The very good characterization of antibodies which are known from the prior art which detect the hyperphosphorylation of the TAU protein is based on the fact that these phosphorylation reactions of the TAU protein are an abnormal state and thus antibodies which recognize this phosphorylated TAU are particularly suitable for detecting pathological conditions.

The techniques known from the literature are based on the fact that abnormally phosphorylated TAU is pathologically relevant and that antibodies are to be prepared and used for detection which recognize this abnormally phosphorylated TAU and in particular exactly the phosphorylation. Furthermore, their binding site to the abnormally phosphorylated TAU is destroyed when dephosphorylation is present.

From the prior art and the cited scientific articles, therefore, no antibody is known so far with which it is possible, and has been invented for this purpose, to detect a fraction which is not phosphorylated at phosphorylation sites hitherto known for pathological processes.

SUMMARY OF THE INVENTION

Starting from the disadvantages of the prior art mentioned above, it is the object of the present invention firstly to provide a monoclonal antibody which specifically recognizes the TAU protein that is non-phosphorylated on the amino acids T175 and/or T181 and/or T231 and secondly to present a hitherto unknown epitope which, due to its property to be the binding site of such an antibody, therefore binds to this non-phosphorylated TAU protein at these binding sites, thereby enabling its identification.

Furthermore, it is the purpose of the present invention to specify a method for preparing the monoclonal antibody and also to develop uses of the monoclonal antibody.

The object mentioned above is achieved in a first aspect of the present invention by the monoclonal antibody 1G2. This monoclonal antibody 1G2 shows high specificity for a human TAU protein which is non-phosphorylated on the phosphorylation sites T175 and/or T181 and/or T231, especially T175 and T181 and T231. The monoclonal antibody 1G2 according to the invention binds, in contrast to antibodies known from the prior art, not to abnormally phosphorylated TAU protein, but recognizes non-abnormal, i.e. natural TAU protein. The binding and therefore the recognition is particularly strong when, for the antibody 1G2 according to the invention, two or all three positions T175 and T181 and T231 are available.

In addition, the monoclonal antibody 1G2 according to the invention binds independently of the mode of action of phosphatases, as are described to some extent in the literature. Moreover, the antibody binds all known isoforms of the TAU protein.

In a second aspect, the object mentioned above is achieved by the hybridoma cell line H-1G2, which is characterized by the deposit with the number DSM ACC3248 of Jul. 15, 2015. This hybridoma cell line produces and secretes the monoclonal antibody 1G2 according to the invention of the isotype IgG2a.

A third aspect of the present invention achieves the object mentioned by the epitope TPP, comprising the amino acids threonine, proline, proline. As amino acid sequence, this epitope TPP is specifically for human proteins, especially for the TAU protein. The amino acids threonine, proline, proline are advantageously flanked on the N-terminus by another basic amino acid which is either R (arginine) or K (lysine). These flanking amino acids are required for the binding to the monoclonal antibody 1G2 according to the invention, since in the TAU protein the KTTP sequence is present twice and the RTTP sequence is present once, which are bound to this antibody.

The flanking effect of these basic amino acids on the binding capacity of the antibody to the sequence TPP indicates that least modifications in the environment of the binding site of the antibody, for example, by further phosphorylation not at the binding sites of the antibody 1G2 but at other amino acids of the TAU protein, of which, for example, the amino acids 184, 195, 198, 199, 202, 205, 208, 210, 212, 214, 217, 235, 237, 238 in the environment of the binding sites, inter alia, are known, could prevent the binding of the antibody 1G2.

In a fourth aspect, the object of the present invention is achieved by a method for preparing a monoclonal antibody against a TAU protein fraction, that is non-phosphorylated at positions T175 and/or T181 and/or T231, especially T175 and T181 and T231, comprising the steps of a) immunizing mammals or in vitro cell cultures with TAU protein which comprises all amino acids and is recombinantly produced and aggregated in vitro, which was phosphorylated in vitro by kinases, to induce a specific immune response against the TAU protein in an adjuvant, b) extracting B-lymphocytes from the mammals or in vitro cell cultures, c) fusion of the B-lymphocytes with a murine myeloma cell line, which is suitable for subsequent selection of fusion cells, to obtain fusion products, d) HAT selection of fusion products in cell culture vessels with specific culture conditions to obtain hybridomas, e) selecting hybridomas which grow under the selection conditions and produce immunoglobulin, due to their reactivity to phosphorylated and non-phosphorylated TAU peptides and also the TAU protein, f) separating the hybridomas at the single cell level to ensure monoclonality of the hybrodima culture, g) culturing the isolated hybridomas as a hybridoma cell line in vitro or in vivo to obtain a monoclonal antibody which recognizes the epitope TPP on a TAU protein.

The TAU protein fraction can in this case be both the complete TAU protein with 441 amino acids (also referred to below as "TAU441"), splicing forms thereof and degraded TAU protein in biological samples and also aggregated TAU protein, which is non-phosphorylated at positions 1175 and/or 1181 and/or T231, especially T175 and T181 and T231.

The immunization of mammals in step a) refers preferably to mice (*Mus musculus*), which are bred and maintained for this purpose.

The immune response specifically mentioned in step a) is particularly understood to mean an immune response based on immunoglobulin G against the TAU protein, which hitherto due to the homology of human and murine TAU protein represented an increased difficulty for the induction of such an immune response. This difficulty could be overcome in the present invention, which was achieved by immunizing with phosphorylated antigens and by this modification the naturally formed tolerance to endogenous antigens, wherein the high homology as a possibility of an existing tolerance is to be seen, is avoided and also with in vitro produced aggregates of the TAU an immune response can be generated which is difficult to induce due to tolerance.

The adjuvant used in step a) supports the development of a T-helper cell response for supporting the raising of specific B cells. It is, for example, a complete Freund's adjuvant.

The step c) murine myeloma cell line, which is suitable for a subsequent selection of fusion cells, preferably represents a B-cell line which itself only incompletely, if at all, forms immunoglobulins and has an effective defect for a HAT-based selection principle. This is, for example, the X63Ag8.653 line. In this step, polyethylene glycol 1500 (mean relative molecular mass 1500) is preferably used.

The fusion products obtained are particularly understood to mean cells which have been produced by fusing cell bodies, cell nuclei and genetic material from the myeloma cell lines used and the isolated B-cells and furthermore show the properties of the unlimited growth of the myeloma cells and of the complete mechanism of purine synthesis and also the production of immunoglobulins of the B-cells.

In the HAT selection in step d), the specific culture conditions are achieved by the use of a medium which promotes the differentiated growth of mouse cells, and in an atmosphere which has been enriched with carbon dioxide at a temperature of 30° C. to 40° C. The hybridomas thus obtained are preferably fusion cells of myeloma cells and B-cells which can grow selectively under the selection pressure of HAT and which are not yet characterized by a specific reactivity or the production of antibodies.

The hybridomas in step e) are selected due to their reactivity toward the TAU peptides, particularly their non-phosphorylated forms and also TAU441.

The concept of the present invention is thereby fulfilled in that the monoclonal antibody 1G2 according to the invention is prepared by the method according to the invention by means of the hybridoma cell line according to the invention and for which the binding to the TAU protein the epitope thereof according to the invention is required.

As an advantage of the present invention, it has been found that the antibody 1G2 according to the invention (and the immunological detection system based thereon) of the first of this type, which compared to the measurements used hitherto of total TAU and phosphorylated TAU (P-TAU), which is proven to be especially phosphorylated at position 181 (Blennow et al. [18]), is now proven to be a fraction which is not phosphorylated at the well-known phosphorylation sites, and which therefore opens new possibilities of extending the diagnostic possibilities existing hitherto.

Accordingly, the present invention is based on an approach which has not previously been described and is developed independently of the known prior art, to detect the TAU protein, which is not subject to the phosphorylation process for the formation of abnormally phosphorylated TAU, which is pathologically relevant.

In a further development of the method according to the invention, the hybridoma cell line H-1G2, as has been described above, is cultured in step g) to obtain the monoclonal antibody 1G2 according to the invention.

In a further aspect, the present invention refers to the use of the monoclonal antibody 1G2 according to the invention to recognize a TAU protein fraction, which is non-phosphorylated at positions T175 and/or T181 and/or T231, especially T175 and T181 and T231. This fraction can be both the complete TAU protein with 441 amino acids, splicing forms thereof and degraded TAU protein in biological samples and also aggregated TAU protein, which is non-phosphorylated at positions T175 and/or T181 and/or T231, especially T175 and T181 and T231. Thus, the antibody is capable of detecting all known TAU forms in biological samples, in particular independently of whether they vary in the phosphorylation/dephosphorylation process in the presence of a phosphate group at the designated phosphorylation sites.

In a preferred development of this use, the monoclonal antibody 1G2 according to the invention is used to detect the TAU protein fraction in human biological samples. This use of the monoclonal antibody 1G2 as a so-called capture antibody offers a high degree of reliability for its specific binding, since—as already described—the binding capacity for phosphorus in the named positions and possibly also the neighbouring positions is a substantial inhibition of this binding. In addition, the monoclonal antibody 1G2 also has a particularly high binding strength, i.e. in the specific case a particularly high avidity, by the possibility of simultaneous binding of two epitopes on a TAU protein.

Another aspect of the present invention relates to the use of the monoclonal antibody 1G2 according to the invention, its humanized form or a molecule with the specific binding properties of the antibody 1G2 according to the invention, at the amino acid sequence TPP for preparing a therapeutic agent for diseases in humans associated with the TAU protein, in which in the therapeutic agent as major constituent, the monoclonal antibody 1G2 according to the invention, its humanized form or a molecule with the specific binding properties of the antibody 1G2 according to the invention at the amino acid sequence TPP, is responsible for the therapeutic effect. In particular, the monoclonal antibody 1G2 according to the invention, its humanized form or a molecule having the specific binding properties of the antibody 1G2 according to the invention at the amino acid sequence TPP can bind to the TAU protein as the most major constituent of those intracellular aggregates which are found in the brain of patients with Alzheimer's disease. When this therapeutic agent is used, the monoclonal antibody 1G2, its humanized form or a molecule having the specific binding properties of the antibody 1G2 according to the invention may be able to block phosphorylation sites for the phosphorylation processes which take place at the amino acid sequence TPP, in particular at positions which initiate processes of hyperphosphorylation or particularly inhibit the physiological binding of the TAU protein to microtubules (Braithwaite et al. [19]).

"Humanized form" of the antibody 1G2 according to the invention is understood to mean that a part of or the complete mouse immunoglobulin consisting of the antibody is converted by means of available genetic methods into human immunoglobulin (Cambridge University Press [20]).

The object described above is achieved in one further aspect of the present invention by an immunochemical detection system comprising
  i) the monoclonal antibody 1G2 according to the invention as capture antibody,
  ii) a second monoclonal antibody against a TAU protein as detection antibody,
  iii) at least one control,
  iv) at least one color and/or detection solution,
  v) at least one stop solution,
  vi) at least one sample buffer,
  vii) at least one wash buffer and
  viii) means for sample preparation.

The term "immunochemical detection system" is understood to mean a combination of constituents (also test kit), which is intended to be used to detect a specific target, in this case a TAU protein fraction, which is non-phosphorylated at important positions of the amino acid sequence.

The monoclonal antibody 1G2 according to the invention can be coated for example on a microtiter plate in this immunochemical detection system. "Capture antibody" in this context signifies that the antibody is immobilized and binds the antigen, i.e. "captures".

The second monoclonal antibody ii) can be a suitable antibody against human TAU protein or a TAU protein of another species and other suitable conjugates of a detection antibody. The second monoclonal antibody is preferably the monoclonal antibody 7E5 (monoclonal antibody IgG3 [kappa], specifically against human TAU, conjugated to horseradish peroxidase). In this context, "detection antibody" signifies that the antigen captured by the capture antibody can be detected with this antibody.

The at least one control iii) serves to demonstrate the functionality of the immunochemical detection system. Said control can be composed of negative controls (e.g. sample buffer) and positive controls (e.g. recombinant TAU protein or synthetic peptides which comprise the epitopes of the antibodies and are linked to each other or linked to each other via a carrier, portioned and lyophilized in sample buffer).

The at least one color and/or detection solution iv) is used depending on the detection selected, e.g. horseradish peroxidase coupled to the detection antibody. In accordance with the invention, the preferred color solution is a potassium citrate buffer pH 3.0 to pH 6.0 with TMB solution (10 mM-100 mM) and peroxide solution (50 mM-500 mM).

The at least one stop solution v) used in the present invention is preferably 0.01 M to 0.5 M sulfuric acid.

The at least one sample buffer vi) is preferably 10 mM to 200 mM phosphate-buffered saline solution pH 7 to pH 8 with 1% to 5% BSA and 0.01% to 0.1% Tween 20.

The at least one wash buffer vii) used according to the invention is 0.1M to 1M Tris pH 7 to pH 8, 0.5M to 5M NaCl, 0.01% to 0.1% Triton X100.

The means for sample preparation viii) is understood to mean, for example, pre-treatment with detergents or by means of physical factors such as heat or ultrasound.

A further aspect for achieving the object named above relates to the use of the immunochemical detection system according to the invention in human diagnostics for investigating blood plasma, blood serum, cerebrospinal fluid or other body fluids on a TAU protein which is non-phosphorylated at positions T175 and/or T181 and/or T231, especially T175 and T181 and T231. This TAU protein fraction can be both the complete TAU protein with 441 amino acids, splicing forms thereof and degraded TAU protein in biological samples and also aggregated TAU protein, which is non-phosphorylated at positions T175 and/or T181 and/or T231, especially T175 and T181 and T231. Thus, all known TAU forms are detected in biological samples, in particular independently of whether they vary in the phosphorylation/dephosphorylation process in the presence of a phosphate group at the designated phosphorylation sites.

Another aspect of the present invention refers to the use of the immunochemical detection system according to the invention in neurochemical dementia diagnostics in humans. Here, this is aimed in particular at the diagnosis of patients with Alzheimer's disease, wherein a differentiation of these patients from other patients without neurodegenerative diseases is made by means of a defined threshold value based on the data determined by a clinical test. In brief, the measurements for the clinical validation of cerebrospinal fluid samples were conducted on very carefully selected and characterized patients with Alzheimer's disease (AD) or mild cognitive impairment (MCI) with Alzheimer's pathology (MCI-AD)—here the positive group—and non-dementia controls—here the negative group. AD/MCI patients were diagnosed and sub-classified corresponding to the most recent recommendations of the National Institute on Aging ((NIA)—in this case the Alzheimer's Association (AA) working groups, Albert et al. [21], McKhann et al. [22]).

Another aspect of the present invention refers to the use of the TPP sequence or phosphorylated form thereof T(Pi)PP for immunizing mammals to raise antibodies against the TPP sequence. This sequence is preferably in the form of peptides or proteins longer than this sequence or also an individual sequence supplemented by, for example, further amino acids. Preferred mammals according to the invention are mice or other suitable animals (particularly rats and rabbits), in order to raise antibodies or other molecules against antigens, which comprise the TPP sequence as binding site of this antibody, against the TPP sequence.

Furthermore, one aspect of the present invention refers to the use of the TPP sequence or phosphorylated from thereof T(Pi)PP for preparing a therapeutic agent or for immunization in humans.

Finally, in one further aspect of the present invention, the use of the TPP sequence or phosphorylated form thereof T(Pi)PP for preparing chemical binders which imitate the structure of the TPP epitope according to the invention, is described.

The aforementioned embodiments and preferences relating to one aspect of the present invention apply correspondingly to the other aspects depicted.

BRIEF DESCRIPTION OF THE DRAWINGS

Other objects, features, advantages and possible applications will become apparent from the following description of exemplary embodiments which are not restrictive of the invention, also with reference to the figures. All the described and/or pictorially illustrated features thereby form the subject matter of the invention, either alone or in any combination, also independently of their summary in the claims or their dependent reference. Shown are:

DETAILED DESCRIPTION OF EMBODIMENTS OF THE INVENTION

Figure 1:
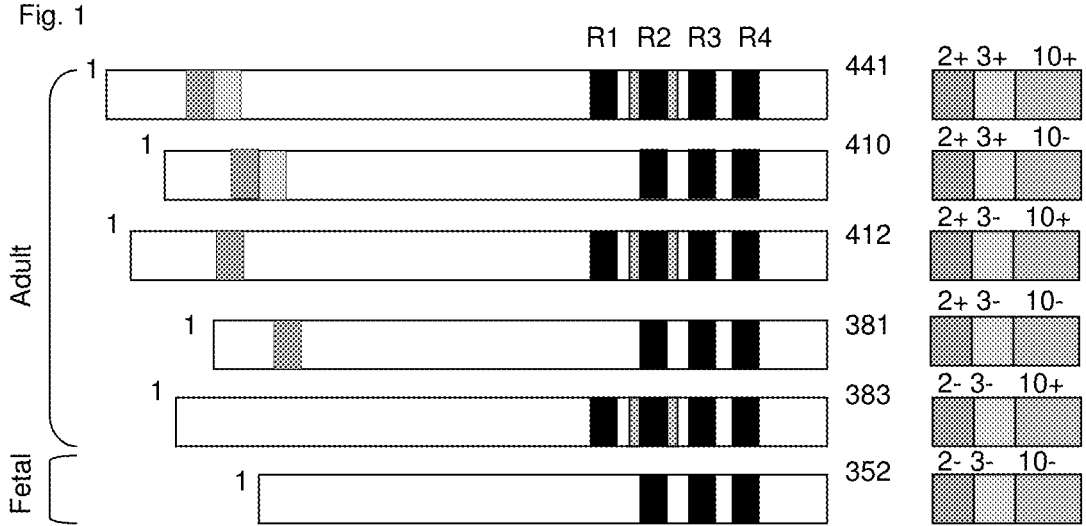
FIG. 1 a schematic representation of TAU isoforms.
Figure 2:
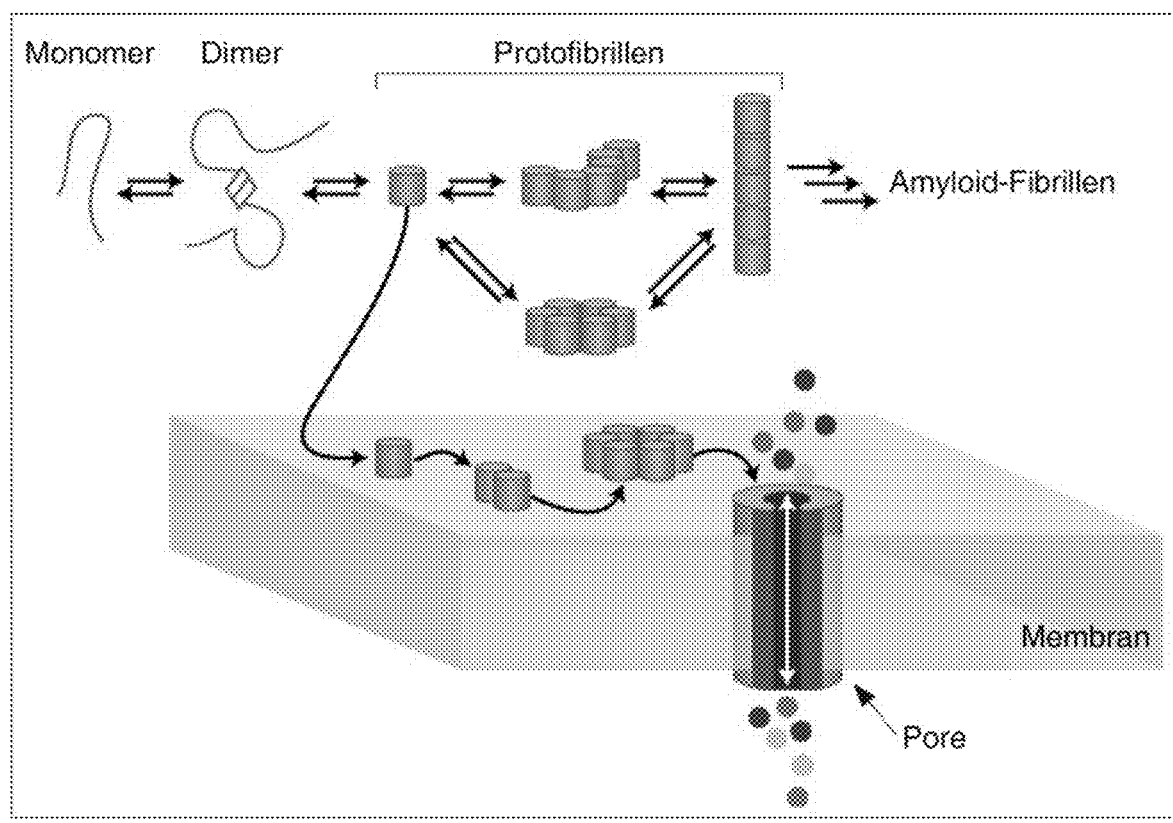
FIG. 2 an aggregation of amyloidogenic proteins and formation of pores in the cell membrane, FIG. 3 a ROC curve analysis of the phosphorus-based TAU ELISA (pTAU rel) and FIG. 4 results of the patient sample analyses.

A specific but non-limiting example of the invention is described below.

Firstly, mice were immunized in Freund's adjuvant with:
TAU protein recombinantly produced and aggregated in vitro,
recombinantly produced TAU protein, which was phosphorylated in vitro by kinases and aggregated in vitro,
synthetic peptides CIPAKTPPAPKTPPS and CKKVAVVRTPPKSPSS, which correspond to the amino acid sequences 170-184 and 223-238 respectively of TAU441, and
synthetic peptides CIPAKTPPAPKTPPS and CKKVAVVRTPPKSPSS, which were phosphorylated at positions I181 and T231.

The B-lymphocytes were taken from mice and fused with the myeloma cell line P3X63 Ag8.653 using 50% polyethylene glycol.

The fusion products were selected by means of HAT selection in cell culture plates according to Littlefield [23]. The primary cell line was characterized by the following tests:
testing on IgG-producing and growth-capable hybridomas,
testing of the reactivity of the IgG produced with the immunogens by ELISA (Enzyme Linked Immunosorbent Assay) and Western Blot (also "immunoblot") and
testing of the reactivity of the IgG produced with the TAU protein by ELISA and Western Blot.

After the immunization and characterization, recombinantly produced TAU protein was phosphorylated by kinases in vitro and aggregated in vitro and the synthetic peptides CIPAKTPPAPKTPPS and CKKVAVVRTPPK- SPSS were phosphorylated at positions T181 and T231, in order to raise suitable antibodies which bind to an amino acid sequence by the phosphorylation sites T181 and T231, and exclusively only if these were present non-phosphorylated.

From the hybridomas generated, those were selected which showed in addition the best reactions with the recombinant TAU protein in ELISA and Western Blot and produced antibodies of the desired IgG isotype.

After immunization, fusion with the myeloma cell line P3X63 Ag8.653 and HAT selection, the hydbridomas developed were cloned and sub-cloned and cultured to give monoclonal hybrodima cells. Expanded monoclonal hybridomas were in turn tested on their ability to produce IgG and their reactivity to the TAU protein by means of ELISA and Western Blot. After successful testing, the hybridomas were protected by freezing $5 \times 10^6$ cells in fetal calf serum +10% dimethyl sulfoxide.

From the variety of resulting hybridomas, the cell line H-1G2 according to the invention was selected and cultured as productive clone.

Production and Protection of MAk and the Hybridoma Cell Line H 1G2 According to the Invention A cell bank of the monoclonal hybridoma cell line H-1G2 according to the invention was initially set up. Batches of the monoclonal antibody 1G2 according to the invention were then produced for use after testing.

Characterization of the Monoclonal Antibody 1G2 According to the Invention

The antibody according to the invention of the monoclonal hybridoma cell line H-1G2 according to the invention was characterized using a mouse hybridoma subtyping kit from Roche. The result of this analysis shows that the antibody has the IgG2a[kappa] isotype.

Western Blot analyses were carried out and showed that the 1G2 antibody according to the invention reacts with TAU441.

Epitope mapping was carried out by Pepscan according to Osman et al. [24]. The antibody 1G2 according to the invention recognized the epitope TPP according to the invention with directly upstream or downstream amino acid K on human TAU protein.

Proof of reactivity in immunoassays with non-phosphorylated TAU protein are evidenced in the working examples below.

Working Examples

1) Phosphorus-Related TAU ELISA

ELISA is an enzyme immunological assay which consists of a capture antibody (monoclonal), a preparation of TAU441 and a POD-labeled detection antibody (monoclonal). Both antibodies bind to different binding domains of TAU441 such that the TAU441 forms a specific bridge between both antibodies (sandwich).

Description of ELISA Procedure

A hundred microlitres of the monoclonal antibody 1G2 according to the invention in 0.05M carbonate buffer pH 9.6 were pipetted into the wells of a microtiter plate (MTP) and stored for 18 hours. The content was aspirated and the free binding sites were saturated using 3% bovine serum albumin solution (assay buffer). 100 μl of TAU441 preparation in a dilution series in assay buffer and 100 cerebrospinal samples (58 Alzheimer's patients, 42 control patients) in duplicate, diluted 1:1 in sample buffer, were placed in the wells of the MTP and incubated with shaking (300 rpm) at room temperature for 120 minutes. After removal with aspiration, 100 μl of detection antibody POD (clone 7E5, specific for TAU441, proprietor AJ Roboscreen GmbH) were pipetted and the plate was incubated at room temperature for 90 minutes. By means of a downstream substrate-POD (horseradish peroxidase) reaction, the amount of bound TAU441 can be determined. Tetramethylbenzidine (TMB) is used as substrate. The signal height is proportional to the amount of TAU441 present. The unknown samples are determined by reference to their signal height on a calibration curve.

Result of the ELISA

The binding of TAU441 on a microtiter plate coated with the 1G2 monoclonal antibody according to the invention was shown in the ELISA. A calibration curve was set up by means of a TAU441 dilution series with the aid of which the cerebrospinal samples measured could be quantified. It was shown that the concentrations calculated of phosphorus-related TAU in the cerebrospinal samples are significantly different between the groups of Alzheimer's patients, including patients in the preclinical stage (109.2±32 pg/ml) and the control patients (62.1±9.1 pg/ml) p<0.001 (Mann-Whitney test).

Figure 4:
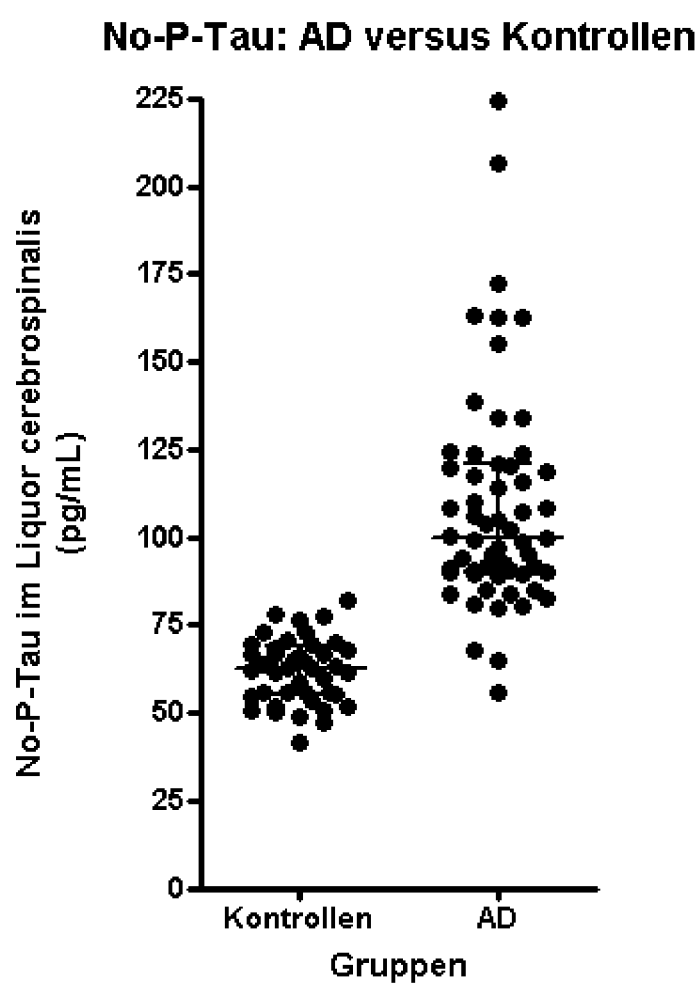

FIG. 4 maps the individual concentrations (each point represents the mean value of the duplicates) and the median values with standard deviations (horizontal bars) (cf. also Table 2).

The patient groups investigated have the characteristics shown in Table 1.

TABLE 1

| Group | Male/Female | Age (years) | MMSE |
| --- | --- | --- | --- |
| AD/MCI (n = 58) with probable AD with a high detection of AD pathophysiological processes (n = 24). possible AD with a high detection of AD pathophysiological processes (n = 8). MCI with high probability of an AD processes (n = 26). | 23/35 | 70.1(±8.2) | 23.1 (±4.1) |
| Controls (n = 42) | 18/24 | 50.3(±14.5) | NA |

Figure 3:
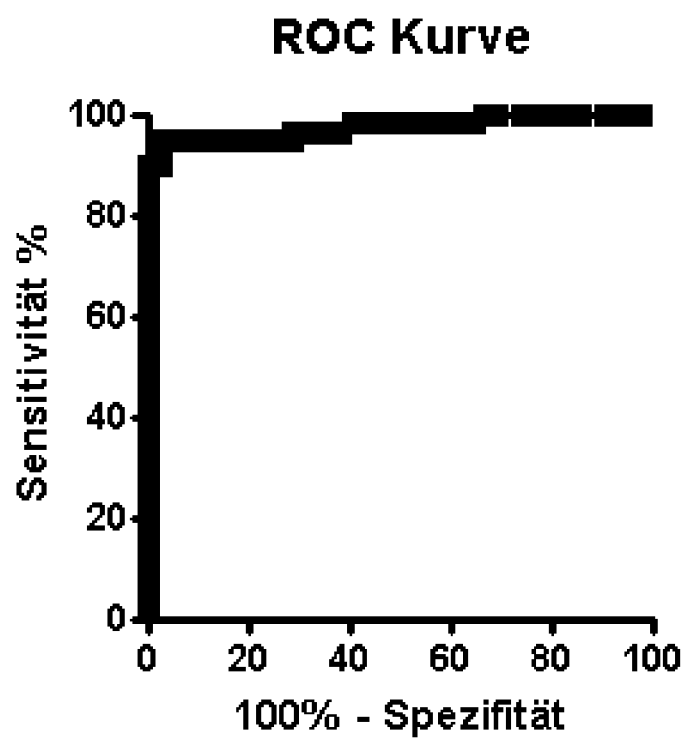

MMSE: Mini-Mental-State-Examination according to Folstein [25]
AD: Alzheimer's Disease
MCI: Mild Cognitive Impairment
NA: Not applicable In the ROC curve analysis and the determination of the diagnostic specificity and sensitivity it could be shown that the ELISA has a high Youden's Index with 0.9245 (range between 0 and 1) at a specificity of 97.6% and a sensitivity of 94.8% and the area under the ROC curve was 0.976, as is shown in FIG. 3. A diagnostically relevant threshold value between 60 pg/ml and 90 pg/ml was found.

TABLE 2

Descriptive statistics of the results of the ELISA measurements in the groups.

| Variable | Group | N | Mean | Standard deviation | Median value | Lower quartile | Upper quartile |
| --- | --- | --- | --- | --- | --- | --- | --- |
| (No-P-T)-AJ Roboscreen | Positive group | 58 | 109.2 | 32.0 | 100.0 | 90.3 | 120.3 |
| (No-P-T)-AJ Roboscreen | Control group | 42 | 62.1 | 9.3 | 62.6 | 55.3 | 68.6 |

Fields of application of the invention are the diagnostics and therapy of neurodegenerative disorders and especially their most common form morbus Alzheimer. The diagnostics can be performed in various body fluids or tissue samples by means of immunochemical test methods. Furthermore, the monoclonal antibody 1G2 according to the invention may be used for histological examinations post mortem in neuropathological diagnostics.

LITERATURE SOURCES

[1] Köhler, G.; Milstein, C.; Continuous Cultures Of Fused Cells Secreting Antibody Of Predefined Specificity; Nature 256 (5517); 495-497; 1975

[2] Lewczuk, P., Kornhuber, J.; Neurochemical dementia diagnostics in Alzheimer's disease: where are we now and where are we going?; Expert Rev Proteomics; 2011 August; 8(4); 447-58

[3] Kosik, K. S., Crandall, J. E., Mufson, E. J., Neve, R. L.; Tau in situ hybridization in normal and Alzheimer brain: localization in the somatodendritic compartment; Ann. Neurol. 26; 352-361, 1989

[4] Goedert, M., Spillantini, M. G., Jakes, R., Rutherford D., Crowther, R. A.; Multiple isoforms of human microtubule-associated protein tau: sequences and localisation in neurofibrillary tangles of Alzheimer's disease; Neuron 3; 519-526; 1989

[5] Neve, R. L., Harris, P., Kosik K. S., Kurnit, D. M., Donlon, A.; Identification of cDNA clones for the human microtubule-associated protein tau and chromosomal localisation of the genes for tau and microtubule-associated protein 2; Molecular Brain Research 1; 271-280; 1986

[6] Goedert, M., Crowther, R. A., Garner, C. C.; Molecular Characterization of Microtubule-Associated Proteins-Tau and Map2; Trends Neurosci 14; 193-199, 1991

[7] Goedert M.; Tau protein and the neurofibrillary pathology of Alzheimer's disease.; Trends Neurosci 16, 460-465; 1993

[8] Hutton, M., Lendon, C. L., Rizzu, P., Baker, M., Froelich, S., Houlden, H., Pickering-Brown, S., Chakraverty, S., Isaacs, A., Grover, A., Hackett, J., Adamson, J., Lincoln, S., Dickson, D., Davies, P., Petersen, R. C., Stevens, M., de Graaff, E., Wauters, E., van Baren, J., Hillebrand, M., Joosse, M., Kwon, J. M., Nowotny, P., Che, L. K., Norton, J., Morris, J. C., Reed, L. A., Trojanowski, J., Basun, H., Lannfelt, L., Neystat, M., Fahn, S., Dark, F., Tannenberg, T., Dodd, P. R., Hayward, N., Kwok, J. B., Schofield, P. R., Andreadis, A., Snowden, J., Craufurd, D., Neary, D., Owen, F., Oostra, B. A., Hardy, J., Goate, A., van Swieten, J., Mann, D., Lynch, T., Heutink, P.; Association of missense and 5'-splice-site mutations in tau with the inherited dementia FTDP-17. Nature 393; 702-705; 1998

[9] Bugiani, O., Murrell, J. R., Giaccone, R., Hasegawa, M., Ghigo, G., Tabaton, M., Morbin, M., Primavera, A., Carella, F., Solaro, C., Grisoli, M., Savoiardo, M., Spillantini, M. G., Tagliavini, F., Goedert, M., Ghetti, B.; Frontotemporal dementia and corticobasal degeneration in a family with a P301S mutation in tau; J Neuropathol Exp Neurol 58; 667-677; 1999

[10] Eidenmüller, J., Fath, T., Hellwig, A., Reed, J., Sontag, E., Brandt, R.; Structural and functional implications of tau hyperphosphorylation: information from phosphorylation-mimicking mutated tau proteins; Biochemistry 39; 13166-13175; 2000

[11] Bancher, C., Brunner, C., Lassmann, H., Budka, H., Jellinger, K., Wiche, G., Seitelberger, F., Grundke-Iqbal, I., Iqbal, K., Wisniewski, H. M.; Accumulation of abnormally phosphorylated tau precedes the formation of neurofibrillary tangles in alzheimer's disease; Brain Res. 477; 90-99; 1989

[12] Friedhoff, P., von Bergen, M., Mandelkow, E. M., Davies, P., Mandelkow, E.; A nucleated assembly mechanism of Alzheimer paired helical filaments; Proc. Natl. Acad. Sci. U.S.A 95; 15712-15717; 1998

[13] Chirita, C. H., Kuret, J.; Evidence for an intermediate in tau filament formation. Biochemistry 43; 1704-1714; 2004

[14] Berriman, J., Serpell, L. C., Oberg, K. A., Fink, A. L., Goedert, M., Crowther, R. A.: Tau filaments from human brain and from in vitro assembly of recombinant protein show cross-beta structure; Proc. Natl. Acad. Sci. U.S.A 100; 9034-9038; 2003

[15] Lashuel, H. A.; Membrane permeabilization: a common mechanism in proteinmisfolding diseases; Sci Aging Knowledge Environ 38; pe28; 2005

[16] Maeda, S., Sahara, N., Saito, Y., Murayama, M., Yoshiike, Y., Kim, H., Miyasaka, T., Murayama, S., Ikai, A., Takashima, A.; Granular tau oligomers as intermediates of tau filaments; Biochemistry 46; 3856-3861; 2007

[17] Caughey, B., Lansbury, P. T.; Protofibrils, pores, fibrils, and neurodegeneration: separating the responsible protein aggregates from the innocent bystanders; Annu. Rev. Neurosci. 26; 267-298; 2003

[18] Blennow, K., Dubois, B., Fagan, A. M., Lewczuk, P., de Leon, M. J., Hampel, H.; Clinical utility of cerebrospinal fluid biomarkers in the diagnosis of early Alzheimer's disease; Alzheimers Dement. 2; 5552-5260; 2014 May

[19] Braithwaite, S. P., Stock, J. B., Lombroso, P. J., Nairn, A. C.; Protein phosphatases and Alzheimer's disease; Prog Mol Biol Transl Sci; 106; 343-379; 2012

[20] Cambridge University Press; Recombinant Antibodies for Immunotherapy. Edited by Melvyn Little. July 2009

[21] Albert, M. S., DeKosky, S. T., Dickson, D., Dubois, B., Feldman, H. H., Fox, N. C., Gamst, A., Holtzman, D. M., Jagust, W. J., Petersen, R. C., Snyder, P. J., Carrillo, M. C., Thies, B., Phelps, C. H.; The diagnosis of mild cognitive impairment due to Alzheimer's disease: recommendations from the National Institute on Aging-Alzheimer's Association workgroups on diagnostic guidelines for Alzheimer's disease.; Alzheimers Dement. 7(3); 270-279; 2011

[23] McKhann, G. M., Knopman, D. S., Chertkow, H., Hyman, B. T., Jack, C. R. Jr., Kawas, C. H., Klunk, W. E., Koroshetz, W. J., Manly, J. J., Mayeux, R., Mohs, R. C., Morris, J. C., Rossor, M. N., Scheltens, P., Carrillo, M. C., Thies, B., Weintraub, S., Phelps, C. H.; The diagnosis of dementia due to Alzheimer's disease: recommendations from the National Institute on Aging-Alzheimer's Association workgroups on diagnostic guidelines for Alzheimer's disease.; Alzheimers Dement. 7(3); 263-269; 2011

[23] Littlefield, J. W.; Selection Of Hybride From Matings Of Fibroblasts In Vitro And Their Presumed Recombinants; Science 145; 709-710,1964

[24] Osman, A. A., Uhlig, H. H., Valdes, I., Amin, M., Mendez, E., Mothes, T.; Monoclonal Antibody Recognizing A Potential Coeliac Toxic Repetitive Pentapeptide Epitope In Gliadins; Eur. J. Gastroenterol. Hepatol. 13; 1189-1193; 2001

[25] Folstein, M. F., Folstein, S. E., McHugh, P. R.; Mini-Mental State (a practical method for grading the state of patients for the clinician); Journal of Psychiatric Research 12; 189-198; 1975

What is claimed is:

1. A monoclonal antibody 1G2.

2. A hybridoma cell line H-1G2, deposited with the DSMZ under deposit number DSM ACC3248.

3. An immunochemical detection system, comprising:
the monoclonal antibody 1G2 according to claim 1 as a capture antibody,
a second monoclonal antibody against a TAU protein as a detection antibody;
at least one control;
at least one color and/or detection solution;
at least one stop solution;
at least one sample buffer; and
at least one wash buffer.

4. The immunochemical detection system according to claim 3, adapted for use in human diagnostics for investigating a body fluid comprising TAU protein.

5. The immunochemical detection system according to claim 4, wherein the body fluid is blood plasma, blood serum, or a cerebrospinal fluid.

6. The immunochemical detection system according to claim 3, adapted for use in neurochemical dementia diagnostics in humans.

7. The immunochemical detection system according to claim 3, wherein the second monoclonal antibody is adapted to detect TAU441.

8. A method for preparing a monoclonal antibody which recognizes a TAU protein or a TAU protein fraction, comprising:
immunizing a mammal or an in vitro cell culture with an adjuvant comprising a phosphorylated TAU protein;
extracting B-lymphocytes from the mammal or the in vitro cell culture,
fusing the B-lymphocytes with a murine myeloma cell line to form a fusion product;
subjecting the fusion product to hypoxanthine-aminopterin-thymidine (HAT) medium selection to obtain hybridomas,
selecting and isolating a single cell hybridoma which is suitable to express the monoclonal antibody which can recognize the TAU protein or TAU protein fraction;
culturing the selected and isolated single cell hybridoma to express the monoclonal antibody,
wherein the TAU protein or TAU protein fraction that can be recognized by the antibody comprises the amino acid sequence CIPAKTPPAPKTPPS (SEQ ID NO.: 1) wherein both T-positions are non-phosphorylated, and
wherein the hybridoma cell line is H-1G2, deposited with the DSMZ under deposit number DSM ACC3248, and the expressed monoclonal antibody is 1G2.

9. The method according to claim 8, wherein the phosphorylated TAU protein of the adjuvant is phosphorylated and aggregated TAU441 protein.

10. The method according to claim 8, wherein the phosphorylated TAU protein has been phosphorylated in vitro by kinases.

11. The method according to claim 8, wherein fusing with the murine myeloma cell line is conducted in polyethylene glycol.

12. The method according to claim 11, wherein the polyethylene glycol has a mean relative molecular mass of 1500.

13. The method according to claim 8, wherein the murine myeloma cell line is X63Ag8.653.

14. The method according to claim 8, wherein the TAU protein or TAU protein fraction that can be recognized by the formed antibody includes TAU441 protein, aggregated TAU441 protein, splicing forms of TAU441 protein, or degraded TAU441 protein.

15. The method of claim 8, wherein the antibody can recognize TAU protein which is non-phosphorylated on positions T175 and T181 and T231.

16. A method for identifying a TAU protein or a TAU protein fraction in a sample, comprising contacting the sample with monoclonal antibody 1G2 according to claim 1, wherein the TAU protein or TAU protein fraction comprises the amino acid sequence CIPAKTPPAPKTPPS (SEQ ID NO.: 1) wherein one or both T-positions are non-phosphorylated.

17. The method according to claim 16, wherein the TAU protein is TAU441 protein which is non-phosphorylated at positions T175 and/or T181.

18. The method according to claim 16, wherein the TAU protein or the TAU protein fraction is identified in a human biological sample.

19. A method of preparing a composition for treatment of a disease in humans associated with the TAU protein, comprising preparing the composition comprising the monoclonal antibody 1G2 according to claim 1 or its humanized form, wherein the antibody interacts with one or two TPP epitopes of the amino acid sequence CIPAKTPPAPKTPPS (SEQ ID NO.: 1).

20. The method of claim 19, wherein the disease is Alzheimer's disease (morbus Alzheimer).

* * * * *

SEQUENCE LISTING

<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 1

Cys Ile Pro Ala Lys Thr Pro Pro Ala Pro Lys Thr Pro Pro Ser
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 2

Cys Lys Lys Val Ala Val Val Arg Thr Pro Pro Lys Ser Pro Ser Ser
1               5                   10                  15